United States Patent [19]

Landscheidt et al.

US005756824A

[11] Patent Number: 5,756,824
[45] Date of Patent: May 26, 1998

[54] PROCESS FOR THE PREPARATION OF CARBAZATES

[75] Inventors: Heinz Landscheidt, Duisburg; Edwin Ritzer, Leverkusen; Alexander Klausener, Köln, all of Germany

[73] Assignee: Bayer Aktiengesellschaft, Leverkusen, Germany

[21] Appl. No.: 730,627

[22] Filed: Oct. 21, 1996

[30] Foreign Application Priority Data

Oct. 27, 1995 [DE] Germany ................ 195 40 073.9

[51] Int. Cl.$^6$ ................................. C07C 261/00
[52] U.S. Cl. ............................................. 560/159
[58] Field of Search ........................... 560/169, 159

[56] References Cited

U.S. PATENT DOCUMENTS

| | | | |
|---|---|---|---|
| 3,894,974 | 7/1975 | Hunter | 260/2.5 |
| 3,956,366 | 5/1976 | Sheppard | 260/482 |
| 4,734,119 | 3/1988 | Diel et al. | |
| 4,739,093 | 4/1988 | Diel et al. | |
| 5,380,828 | 1/1995 | Ravichandran | 534/751 |

FOREIGN PATENT DOCUMENTS

| | | | |
|---|---|---|---|
| 0103400 | 3/1984 | European Pat. Off. | |
| 0106282 | 4/1984 | European Pat. Off. | |
| 38-14720 | 8/1963 | Japan | 560/169 |
| 46-37570 | 11/1971 | Japan | 560/169 |

OTHER PUBLICATIONS

Adams, Chemical Reviews, vol. 65, pp. 567–602, 1965.

N. Rabjohn, The Synthesis and Reactions of Disazodicarboxylates[1], J. Am. Chem. Soc., vol. 70, pp. 1181–1183, (1948).

C.H. Scaman, et al., Inhibition of Cytoplasmic Aspartate Aminotransferase from Porcine Heart by R and S Isomers of Aminooysuccinate and Hydrazinosuccinate*, The Journal of Biological Chemistry, vol. 266, No. 9, pp. 5525–5533, (1991).

Berichte der Deutschen, Gesellschaft, Bd. 47, No. 2, 1914, Seiten 2183–2188, XP000617234, Diels O: "Darstellung und Neue Reaktionen der Hydrazin–Monocarbonsaeureester".

A.-A.G. Shaikh, et al., Dialkyl and Diaryl Carbonates by Carbonate Interchange Reaction with Dimethyl Carbonate†, Ind. Eng. Chem. Res., 31, pp. 1167–1170, (1992).

*Primary Examiner*—Michael L. Shippen
*Attorney, Agent, or Firm*—Sprung Kramer Schaefer & Briscoe

[57] ABSTRACT

Alkyl carbazates of the formula $R^1$—O—CO—NH—$NH_2$ (I) are prepared in an advantageous manner by reacting an alkyl carbazate of the formula $R^2$—O—CO—NH—$NH_2$ (II) with alcohols of the formula $R^1$—OH (III) in the presence of a catalyst, where the symbols used in the formulae are as defined in the description.

10 Claims, No Drawings ethyl carbazates by reacting unsubstituted $C_1$–$C_4$-alkyl carbazates with optionally substituted $C_2$–$C_{20}$-alkyl alcohols in the presence of a catalyst.

PROCESS FOR THE PREPARATION OF CARBAZATES

The present invention relates to a process for the preparation of optionally substituted $C_2$–$C_{20}$-alkyl carbazates by reacting unsubstituted $C_1$–$C_4$-alkyl carbazates with optionally substituted $C_2$–$C_{20}$-alkyl alcohols in the presence of a catalyst.

Carbazates are employed as intermediates in the preparation of plant protection products and pharmaceuticals. They are used in particular for peptide syntheses (see EP-A 106 282). According to J. Biol. Chem. 266, 5525 (1991) it is possible from benzyl carbazate to prepare hydrazinosuccinate, an aspartate amino-transferase inhibitor. EP-A 143 078 describes the use of benzyl carbazate for the preparation of plant protection products.

Carbazates are generally obtained by reacting chloroformic esters with hydrazine. For instance, Chem. Ber. 92, 1478 (1959) describes the reaction of benzyl chloroformate with hydrazine to form benzyl carbazate in this case, however, the preparation of the precursors employs phosgene and is comparatively complex.

According to another method, symmetrical dialkyl carbonates are reacted with hydrazine (see J. Am. Chem. Soc. 70, 1181 (1948)). Here again the preparation of the precursors, especially when they are higher carbonates, is difficult or impossible. Dibenzyl carbonate, for example, can only be obtained in a highly impure form, since in that case benzyl chloride is always obtained as by-product. This procedure is also not very economical, since the alcohol by-product must either be disposed of or recovered by an additional isolation step.

There therefore continues to be a need for a process for the reliable, readily practicable and economic preparation of carbazates.

A process has now been found for the preparation of alkyl carbazates of the formula (I)

$$R^1\text{—O—CO—NH—NH}_2 \qquad (I),$$

in which $R^1$ represents optionally substituted, straight-chain or branched $C_2$–$C_{20}$-alkyl, optionally substituted $C_3$–$C_6$-cycloalkyl or optionally substituted $C_6$–$C_2$-aryl, which comprises reacting an alkyl carbazate of the formula (II)

$$R^2\text{—O—CO—NH—NH}_2 \qquad (II),$$

in which $R^2$ represents straight-chain or branched, unsubstituted $C_1$–$C_4$-alkyl, with alcohols of the formula (III)

$$R^1\text{—OH} \qquad (III),$$

in which $R^1$ is as defined for formula (I), in the presence of a catalyst.

Straight-chain and branched unsubstituted $C_1$–$C_4$-alkyl carbazates of the formula (II) are readily available on the industrial scale by reacting dialkyl carbonates of the formula (IV)

$$R^2\text{—O—CO—O—}R^2 \qquad (IV),$$

in which $R^2$ is as defined for formula (II), with hydrazine (see e.g. Ber. Chem. Ges. 47, 2183 to 2188 (1914)). Dimethyl carbonate can also be prepared on the industrial scale without the use of phosgene, for example by oxidizing carbon monoxide with oxygen in the presence of methanol and catalysts (see e.g. EP-A 365 083).

The alcohol liberated in the course of this reaction can be trapped, so that the reaction according to the invention can be carried out overall without expensive consumption of chemicals and without the production of relatively large amounts of waste products.

Where $R^1$ in the formulae (I) and (III) is substituted straight-chain or branched $C_2$–$C_{20}$-alkyl, substituted $C_3$–$C_6$-cycloalkyl or substituted $C_6$–$C_{12}$-aryl, examples of suitable substitutes are halogen, hydroxyl, the group X—$R^3$ (where X = oxygen or sulfur and $R^3$ = straight-chain or branched $C_1$–$C_4$-alkyl), the group COO$R^4$ (where $R^4$ = $C_1$–$C_4$-alkyl), the group NR$^5$R$^6$ (where $R^5$ and $R^6$ = independently of one another in each case $C_1$–$C_4$-alkyl) and $C_3$–$C_6$-cycloalkyl which is optionally substituted by straight-chain or branched $C_1$–$C_4$-alkyl groups. Where $R^1$ in the formulae (I) and (III) is substituted straight-chain or branched $C_2$–$C_{20}$-alkyl or substituted $C_3$–$C_6$-cycloalkyl, other suitable substitutes are optionally substituted $C_6$–$C_{14}$-aryl and optionally substituted $C_6$–$C_{14}$-aryloxy, 1-piperidinyl, 1-morpholinyl and 1-pyrrolidinyl.

The aryl radicals, including those in the form of substitutes of alkyl and cycloalkyl and in the form of aryloxy substitutes, are preferably phenyl, naphthyl or biphenyl.

Examples of suitable substitutes for aryl and aryloxy radicals are $C_1$–$C_4$-alkyl, $C_1$–$C_4$-alkoxy, di-$C_1$–$C_4$-alkylamino, nitro and halogen.

All of the substitutes mentioned can be present one or more times. It is also possible for two or more different substitutes to be present alongside one another.

$R^1$ preferably denotes straight-chain or branched $C_5$–$C_{14}$-alkyl or $C_3$–$C_6$-cycloalkyl which is optionally substituted by fluorine, chlorine, the group X—$R^3$ (as defined above), unsubstituted $C_3$–$C_6$-cycloalkyl and/or optionally $C_1$–$C_4$-alkyl-, $C_1$–$C_4$alkoxy-, fluorine- and/or chlorine-substituted phenyl, and unsubstituted phenyl.

$R^1$ particularly preferably denotes straight-chain $C_5$–$C_{18}$-alkyl which is optionally substituted by phenyl, or $C_3$–$C_6$-cycloalkyl which is optionally substituted by $C_1$–$C_2$-alkyl.

$R^1$ very particularly preferably denotes t-butyl, pentyl, i-pentyl, hexyl, dodecyl, hexadecyl, octadecyl, benzyl, cyclopropyl, cyclopropylmethyl, cyclobutyl, cyclopentyl or cyclohexyl.

In the formulae (II) and (IV) $R^2$ preferably represents methyl or ethyl.

To carry out the process according to the invention it is possible for the respective alkyl carbazate of the formula (II), for example methyl carbazate, to be reacted with the respective alcohol of the formula (III), for example in a molar ratio of from 0.5 to 20:1, preferably from 0.9 to 5:1, very particularly preferably from 0.9 to 1.5:1, optionally with the addition of a solvent which is stable under the reaction conditions. Examples of suitable solvents are hydrocarbons, ethers and acid amides, such as cyclohexane, toluene, chlorobenzene, ethylene glycol dimethyl ether, diethylene glycol dimethyl ether and dimethylformamide. It is advantageous to employ crude alkyl carbazate of the formula (II) as is obtained, for example, in the reaction of dialkyl carbonates of the formula (IV) with hydrazine, without further purification or intermediate isolation.

Catalysts which are suitable are a very wide variety of basic compounds. For reasons of increased ease of separation after the end of the process according to the invention, preference is given to solid basic compounds as catalyst. Examples of catalysts are alkali metal hydroxides such as lithium hydroxide, sodium hydroxide and potassium hydroxide, alkaline earth metal hydroxides, such as calcium hydroxide, alkali metal and alkaline earth metal carbonates and hydrogen carbonates, such as lithium carbonate, sodium carbonate, potassium carbonate, magnesium carbonate, calcium carbonate, sodium hydrogen carbonate and potassium hydrogen carbonate, and alkali metal and alkaline earth metal alcoholates, such as lithium methanolate and sodium methanolate. When alkali metal and alkaline earth metal alcoholates are used, in order to avoid the formation of unwanted by-products it is preferred to select those which are derived from the particular alcohol of the formula (III) which is employed or from the alcohol of the formula $R^2$—OH which is formed as by-product.

As catalysts it is also possible to employ amino compounds, for example bicyclic amino compounds such as 1,5-diazabicyclo[4.3.0]non-5-ene and 1,8-diazabicyclo-[5.4.0]undec-7-ene, titanium compounds such as titanium (IV) isopropylate and tin compounds such as dibutyltin oxide and dimethyltin didodecanoate.

The catalyst can be employed, for example, in amounts of from 0.001 to 10% by weight, based on alkyl carbazate of the formula (II) employed.

The reaction according to the invention can be carried out, for example, at temperatures from 50° to 250° C., preferably from 80° to 180° C., and under a pressure of from 0.1 to 10 bar, preferably atmospheric pressure.

The alcohol of the formula $R^2$—OH which is formed in the course of the reaction according to the invention is preferably distilled off during the actual reaction. This procedure can optionally be assisted by the addition of an azeotrope former, for instance an aromatic hydrocarbon, especially toluene.

After the end of the reaction according to the invention it is possible to work up the reaction mixture by, for example, separating off the catalyst, for example by filtration or by extraction with water. Any excess alcohol present can be separated off by distillation if appropriate. The crude reaction product which remains can optionally be purified further with the aid of techniques known per se, for example by distillation or crystallization.

It is extremely surprising that it is possible with the process according to the invention, in a technically simple manner and with the avoidance of wastes and chemicals which are difficult to handle, to prepare carbazates, especially those having radicals on the carbonyloxy group which are relatively large and/or of relatively complex construction. Indeed, from the prior art it is known that amino groups located adjacent to carbonyl groups (an arrangement as is present inter alia in the starting compounds of the formula (II) for the reaction according to the invention) react with alcohols to form urethanes or carbonates (see e.g. U.S. Pat. No. 2,834,799, U.S. Pat. No. 2,837,561 and EP-A 13 957).

EXAMPLES

Example 1

45 g of methyl carbazate were mixed with 54.0 g of benzyl alcohol and 2.0 g of potassium carbonate. The mixture thus obtained was heated at 130° C. for 3 hours. The methanol which forms during this time was distilled off. The reaction mixture was worked up by separating off the catalyst by filtration, after cooling to room temperature, and distilling off the remaining benzyl alcohol. The residue (46.5 g) comprised 97% by weight of benzyl carbazate according to analysis by gas chromatography. The melting point of the product was 69° C., and the $^1$H-NMR spectrum, recorded in deuterochloroform, showed characteristic absorptions at δ=3.5; 5.15; 6.35 and 7.25–7.4 ppm.

What is claimed is:

1. A process for the preparation of an alkyl carbazate of the formula (I)

$R^1$—O—CO—NH—NH$_2$ (I), in which $R^1$ represents straight chain $C_5$–$C_{18}$-alkyl or $C_3$–$C_6$-cycloalkyl which is optionally substituted by one or more members of the group consisting of fluorine, chlorine, the group X—$R^3$, $C_3$–$C_6$-cycloalkyl, unsubstituted phenyl and phenyl which is substituted with one or more of $C_1$–$C_4$-alkyl-, $C_1$–$C_4$-alkoxy-, fluorine-, chlorine-, wherein X represents oxygen or sulfur and $R^3$ represents straight-chain or branched $C_1$–$C_4$-alkyl, which comprises reacting an alkyl carbazate of the formula (II)

$R^2$—O—CO—NH—NH$_2$ (II), in which $R^2$ represents straight-chain or branched, unsubstituted $C_1$–$C_4$-alkyl, with an alcohol of the formula (III)

$R^1$—OH (III), in which $R^1$ is as defined for formula (I), in the presence of a catalyst.

2. The process as claimed in claim 1, wherein, in the formulae (I) and (III), $R^1$ represents straight-chain $C_5$–$C_{18}$-alkyl which is optionally substituted by phenyl, or $C_3$–$C_6$-cycloalkyl which is optionally substituted by $C_1$–$C_2$-alkyl.

3. The process as claimed in claim 1, wherein $R^1$ represents straight-chain or branched $C_5$–$C_{18}$-alkyl or $C_3$–$C_6$-cycloalkyl which is unsubstituted or substituted by fluorine, chlorine, the group X—$R^3$ (as defined in claim 2), unsubstituted $C_3$–$C_6$-cycloalkyl or unsubstituted phenyl or phenyl substituted by $C_1$–$C_4$-alkyl, $C_1$–$C_4$-alkoxy, fluorine or chlorine.

4. The process as claimed in claim 1, wherein $R^1$ represents straight-chain $C_5$–$C_{18}$-alkyl which is optionally substituted by phenyl, or $C_3$–$C_6$-cycloalkyl which is optionally substituted by $C_1$–$C_2$-alkyl.

5. The process as claimed in claim 1, wherein $R^1$ represents pentyl, I-pentyl, hexyl, dodecyl, hexadecyl, octadecyl, benzyl, cyclopropyl, cyclopropylmethyl, cyclobutyl, cyclopentyl or cyclohexyl.

6. The process as claimed in claim 1, wherein the alkyl carbazate of the formula (II) employed is any one in which $R^2$ represents methyl or ethyl.

7. The process as claimed in claim 1, wherein an alkyl carbazate of the formula (II) and an alcohol of the formula (III) are employed in a molar ratio of from 0.5 to 20:1.

8. The process as claimed in claim 1, wherein the catalyst employed is an alkali metal hydroxide, an alkaline earth metal hydroxide, an alkali metal or alkaline earth metal carbonate or hydrogen carbonate or an alkali metal or alkaline earth metal alcoholate, amino compound, titanium compound or tin compound.

9. The process as claimed in claim 1, wherein a crude alkyl carbazate of the formula (II) is employed as is obtainable in the reaction of dialkyl carbonates of the formula (IV)

$R^2$—O—CO—O—$R^2$ (IV), in which $R^2$ is as defined in claim 1 for formula (II), with hydrazine without further purification or intermediate isolation.

10. The process as claimed in claim 1, wherein the catalyst is employed in amounts of from 0.001 to 10% by weight, based on the alkyl carbazate of the formula (II), and the reaction is carried out at from 50° to 250° C.

* * * * *